United States Patent [19]

Lüthy et al.

[11] Patent Number: 4,514,566
[45] Date of Patent: Apr. 30, 1985

[54] 5-OXO-3-THIAZOLINE OXIME AND 2-OXO-5,6-DIHYDRO-2H-1,4-THIAZINE OXIME DERIVATIVES

[75] Inventors: Christoph Lüthy, Schwerzenbach; Paul Winternitz, Greifensee, both of Switzerland

[73] Assignee: Hoffmann-La Roche Inc., Nutley, N.J.

[21] Appl. No.: 546,212

[22] Filed: Oct. 27, 1983

Related U.S. Application Data

[62] Division of Ser. No. 257,072, Apr. 24, 1981, Pat. No. 4,427,687.

[51] Int. Cl.³ .......................................... C07D 277/04
[52] U.S. Cl. .................................... 544/56; 548/147; 548/197
[58] Field of Search .................. 544/56; 548/147, 197; 424/246, 270

[56] References Cited

U.S. PATENT DOCUMENTS 3,767,662 10/1973 Kay .................................. 260/306.7
3,790,566 2/1974 Bellina ............................ 260/243 R
3,894,150 7/1975 Durden ............................ 424/246
4,071,627 1/1978 Durden ............................ 424/246
4,255,436 3/1981 Winternitz ........................ 424/270

FOREIGN PATENT DOCUMENTS 1357711 6/1974 United Kingdom ............ 260/306.7

Primary Examiner—Henry R. Jiles
Assistant Examiner—J. G. Mullins
Attorney, Agent, or Firm—Jon S. Saxe; George M. Gould; John J. Maitner

[57] ABSTRACT

Carbamoyl-oxime compounds of the formula

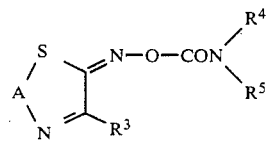

wherein A, $R^3$, $R^4$ and $R^5$ are as hereinafter set forth, a process for their preparation, pesticidal compositions containing one or more of these compounds as the active ingredient, methods of use of such compositions for the control of pests, particularly insects, mites, nematodes and molluscs, and intermediates for the production of such compounds are described.

6 Claims, No Drawings

5-OXO-3-THIAZOLINE OXIME AND 2-OXO-5,6-DIHYDRO-2H-1,4-THIAZINE OXIME DERIVATIVES

This is a division of application Ser. No. 257,072 filed Apr. 24, 1981, now U.S. Pat. No. 4,427,687.

DETAILED DESCRIPTION OF THE INVENTION this invention is directed to carbamoyl oximes of the formula

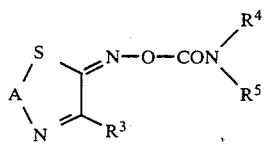

wherein A is a group (a) or (b)

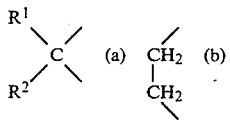

$R^1$ and $R^2$ are hydrogen, lower alkyl or cycloalkyl, or together with the carbon atom to which they are attached a 4- to 6-membered, saturated hydrocarbon ring, $R^3$ is hydrogen, lower alkyl or cycloalkyl, $R^4$ is hydrogen and $R^5$ is lower alkyl, lower alkenyl or cycloalkyl, or $R^4$ is lower alkyl and $R^5$ is lower alkyl, lower alkylcarbonyl, tri(lower alkyl)silyl or a group (c)

$R^6$ is alkyl, lower haloalkyl; phenyl, phenyl substituted with halogen, lower alkyl and/or trifluoromethyl; or a group (d) or (e)

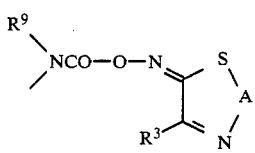

$R^7$ and $R^8$ are lower alkyl or lower haloalkyl, or together with the nitrogen atom to which they are attached a piperidino or morpholino group, $R^9$ is lower alkyl and m is 1 or 2.

The compounds of formula I are useful for the control of pests and are especially suitable for the control of insects, mites, nematodes and molluscs. Accordingly, the invention is also directed to pesticidal compositions which contain one or more of the compounds of formula I as the active ingredient.

This invention is also directed to processes for the preparation of these pesticidal compositions as well as methods for their use.

As used herein the term "lower alkyl" denotes both straight-chain and branched-chain hydrocarbon groups containing from 1 to 4 carbons such as methyl, ethyl, n-propyl, isopropyl, n-butyl, isobutyl and tert.-butyl. This connotation also applies to those groups containing lower alkyl moieties such as lower alkylcarbonyl and lower haloalkyl. The term "lower alkenyl" denotes straight-chain and branched-chain unsaturated hydrocarbon groups containing from 2 to 5 carbon atoms such as vinyl, allyl, butenyl, pentenyl, and the like. The term "halogen" includes fluorine, chlorine, bromine and iodine. The term "cycloalkyl" includes cyclic groups of from 3 to 6 carbon atoms such as cyclopropyl, cyclobutyl, cyclopentyl and cyclohexyl. When two or more substituents are present in a substituted phenyl group, the substituents can be the same or different.

The invention also encompasses the syn- and anti-forms of the compounds of formula I, of which the syn(Z)-forms are preferred. Since asymmetric carbon atoms can be present, optical antipodes exist in such cases. By the presence of the double bond in the compounds of formula I wherein $R^5$ denotes lower alkenyl, geometric isomers additionally occur for such compounds. Formula I is accordingly intended to include all of these possible isomeric forms.

Compounds of formula I in which $R^1$ and $R^2$ is lower alkyl such as methyl or ethyl, and particularly methyl are preferred. Moreover, the total number of carbon atoms in the substituents $R^1$ and $R^2$ of these compounds preferably does not exceed 4.

Also preferred are compounds of formula I in which $R^1$ and $R^2$ together with the carbon atom to which they are attached is a 4- to 6-membered, saturated hydrocarbon ring, particularly a 5- to 6-membered ring.

Compounds of formula I in which $R^1$ and $R^2$ each denote hydrogen or lower alkyl are preferred.

Compounds of formula I in which A is group (a), and $R^3$ is lower alkyl such as methyl are preferred.

Also preferred are compounds of formula I in which A is the group (b), and $R^3$ is lower alkyl, particularly isopropyl.

Compounds of formula I in which $R^4$ is lower alkyl, particularly methyl, are preferred.

Compounds of formula I are preferred where $R^5$ is lower alkyl, lower alkenyl, cycloalkyl, lower alkylcarbonyl or tri(lower alkyl)silyl, particularly methyl, allyl, cyclopropyl, acetyl, or trimethylsilyl or tri(tert.-butyl)silyl resectively.

Also preferred are compounds of formula I where $R^5$ is the group (c), and $R^6$ is alkyl containing up to 8 carbon atoms.

Also preferred are compounds of formula I where $R^6$ in group (c) is lower haloalkyl, particularly trichloromethyl, dichlorofluoromethyl or trifluoromethyl.

Compounds of formula I in which $R^5$ is lower alkyl, particularly methyl, and $R^4$ is hydrogen are preferred.

Especially preferred compounds of formula I are:

5-Oxo-2,2,4-trimethyl-3-thiazoline O-(methylcarbamoyl)oxime and 2-oxo-5,6-dihydro-3-isopropyl-2H-1,4-thiazine O-(methylcarbamoyl)oxime.

Further examples of compounds of formula I are:

5-Oxo-4-methyl-3-thiazoline O-(methylcarbamoyl)oxime,

5-Oxo-2-cyclopropyl-2,4-dimethyl-3-thiazoline O-(methylcarbamoyl)oxime, 5-oxo-2,2,4-trimethyl-3-thiazoline O-(allylcarbamoyl)oxime, 5-oxo-2,2,4-trimethyl-3-thiazoline O-(cyclopropylcarbamoyl)oxime, 5-oxo-2,2,4-trimethyl-3-thiazoline O-(N-acetyl-N-methylcarbamoyl)oxime, 5-oxo-2,2,4-trimethyl-3-thiazoline O-(N-methyl-N-trimethylsilylcarbamoyl)oxime, 5-oxo-2,2,4-trimethyl-3-thiazoline O-(N-methyl-N-(methylsulphenyl)carbamoyl)oxime, 5-oxo-2,2,4-trimethyl-3-thiazoline O-(N-methyl-N-(methylthiosulphenyl)carbamoyl)oxime, 5-oxo-2,2,4-trimethyl-3-thiazoline O-(N-isopropylthiosulphenyl-N-methylcarbamoyl)oxime, 5-oxo-2,2,4-trimethyl-3-thiazoline O-(N-tert.-butylthiosulphenyl)-N-methylcarbamoyl)oxime, 5-oxo-2,2,4-trimethyl-3-thiazoline O-(N-methyl-N-(n-octylthiosulphenyl)carbamoyl)oxime, 5-oxo-2,2,4-trimethyl-3-thiazoline O-(N-trichloromethylsulphenyl-N-methylcarbamoyl)oxime, 5-oxo-2,2,4-trimethyl-3-thiazoline O-(N-dichlorofluoromethylsulphenyl-N-methylcarbamoyl)oxime, 5-oxo-2,2,4-trimethyl-3-thiazoline O-(N-trifluoromethylsulphenyl-N-methylcarbamoyl)oxime, 5-oxo-2,2,4-trimethyl-3-thiazoline O-(N-[(4-chlorophenyl)sulphenyl]-N-methylcarbamoyl)oxime, 5-oxo-2,2,4-trimethyl-3-thiazoline O-(N-methyl-N-[(2-methylphenyl)sulphenyl]carbamoyl)oxime, 5-oxo-2,2,4-trimethyl-3-thiazoline O-(N-methyl-N-[(4-methylphenyl)sulphenyl]carbamoyl)oxime, 5-oxo-2,2,4-trimethyl-3-thiazoline O-(N-[(3,4-dimethylphenyl)sulphenyl]-N-methylcarbamoyl)oxime, 5-oxo-2,2,4-trimethyl-3-thiazoline O-(N-methyl-N-[(3-trifluoromethylphenyl)sulphenyl]carbamoyl)oxime, 5-oxo-2,2,4-trimethyl-3-thiazoline O-(N-[(4-tert.-butylphenyl)thiosulphenyl]-N-methylcarbamoyl)oxime, 5-oxo-2,2,4-trimethyl-3-thiazoline O-(N-dimethylaminosulphenyl-N-methylcarbamoyl)oxime, 5-oxo-2,2,4-trimethyl-3-thiazoline O-(N-di(2-chloroethyl)aminosulphenyl-N-methylcarbamoyl)oxime and N,N'-bis-(2,2,4-trimethyl-3-thiazoline-5-O-(methylcarbamoyl)oximino)-disulphide.

The compounds of this invention are prepared by the processes described below.

PROCEDURE A

An oxime of the formula

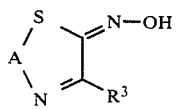

II wherein A and $R^3$ are as defined earlier,
in reacted with an isocyanate of the formula $$R^5-N=C=O \quad \text{III}$$

wherein $R^5$ is as defined earlier,
conveniently in the presence of a diluent and, optionally, in the presence of a catalyst.

Procedure A affords compounds of formula I wherein $R^4$ is hydrogen, and $R^5$ is lower alkyl, lower alkenyl or cycloalkyl.

Diluents for the reaction of Procedure A include inert organic solvents. Preferred solvents are ethers and ether-like compounds such as 1,2-dimethoxyethane, tetrahydrofuran and dioxan; ketones such as diethyl ketone, particularly acetone and methyl ethyl ketone; nitriles such as propionitrile, particularly acetonitrile; formamides such as dimethylformamide; and halogenated hydrocarbons such as methylene chloride, carbon tetrachloride and chloroform.

Preferred catalysts are tertiary bases such as triethylamine, pyridine and 1,4-diazabicyclo[2.2.2]octane; and organic tin compounds such as dibutyl tin diacetate.

The reaction temperatures can vary over a wide range. In general, the reaction is carried out at a temperature between 0° C. and 100° C., and, preferably, between 20° C. and 50° C. When a solvent is present, the reaction is conveniently carried out at the boiling point of the solvent used.

The reaction is preferably carried out using an excess of isocyanate of formula III. The compounds of formula I wherein $R^4$ represents hydrogen are isolated by distilling the solvent and working up the residue by standard procedures.

PROCEDURE B

An oxime of formula II, as defined earlier, is reacted with a carbamoyl halide of the formula

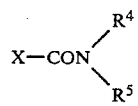

IV wherein $R^4$ and $R^5$ are as defined earlier, and X is a halogen atom, conveniently in the presence of a diluent and an acid-binding agent.

Diluents for the reaction of Procedure B include inert organic solvents. Preferred solvents are those mentioned for Procedure A above.

The reaction is conveniently carried out in the presence of an acid-binding agent. While any inorganic and organic acid-binding agents can be used, the preferred acid-binding agents are sodium hydride; alkali carbonates such as sodium carbonate, potassium carbonate and sodium bicarbonate; lower tertiary alkylamines, cycloalkylamines and arylalkylamines such as triethylamine and dimethylbenzylcyclohexylamine; pyridine and diazabicyclooctane.

The reaction temperatures can vary over a wide range. In general, the reaction is carried out at a temperature between 0° C. and 100° C., and, preferably, between 0° C. and 40° C.

The reaction is preferably carried out using 1 to 2 mol of carbamoyl halide of formula IV for each mol of the oxime of formula II. A slight excess of acid-binding agent (up to ca. 30 weight percent) is advantageous. The isolation of compounds of formula I is carried out using standard procedures.

PROCEDURE C

An oxime of formula II, as defined above, is reacted with phosgene and subsequently an amine of the formula

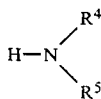

V wherein $R^4$ and $R^5$ are as defined above,
conveniently in the presence of a diluent and an acid-binding agent.

Diluents for the reaction of Procedure C include inert organic solvents. Preferred solvents are ethers and ether-like compounds such as 1,2-dimethoxyethane, tetrahydrofuran and dioxan; nitriles such as acetonitrile; formamides such as dimethylformamide; and hydrocarbons such as toluene.

The reaction is conveniently carried out in the presence of an acid-binding agent. While any inorganic and organic acid-binding agents can be used, the preferred acid-binding agents are those mentioned for Procedure B above.

The reaction temperatures can vary over a wide range. In general, the reaction is carried out at a temperature between 0° C. and 100° C., and, preferably, between 0° C. and 40° C.

The reaction procedure is conveniently carried out as a one-pot process. Phosgene is reacted with the oxime of formula II and then the amine of formula V is added to the reaction mixture. It has been found to be advantageous to employ for 1 mol of oxime of formula II 1 to 1.5 mol of phosgene and 1 to 1.5 mol of amine of formula V. Further, a slight excess of acid-binding agent, e.g. up to about 30 weight precent, is preferably used. The isolation of the compounds of formula I is carried out using standard procedures.

PROCEDURE D

A carbamoyl oxime of the formula

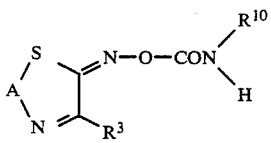    I' wherein A and $R^3$ are as defined earlier, and $R^{10}$ is lower alkyl,
which may be obtained according to one of the above process variants, is reacted with a sulphenyl chloride of the formula Cl—S$_m$—R$^{11}$    VI wherein m is 1 or 2, and $R^{11}$ is as defined earlier for $R^6$ or chlorine, conveniently in the presence of a diluent and an acid-binding agent.

Procedure D affords compounds of formula I wherein $R^4$ is lower alkyl, and $R^5$ is a group (c).

The diluents and acid-binding agents utilized in this reaction are those mentioned above in connection with Procedures A and B. The reaction is generally carried out at a temperature between 0° C. and 100° C., and, preferably, between 0° C. and 50° C.

Where a sulphenyl chloride of formula VI wherein $R^{11}$ is chlorine is used in this reaction, the starting materials are preferably used in about stoichiometric amounts, i.e. for one mol of the sulphenyl chloride of formula VI there are preferably used about 2 mol of the carbamoyl oxime of formula I'.

The isolation of the compounds of formula I is carried out using standard procedures.

The products prepared according to the above-noted procedures are normally obtained as a mixture of two or more isomers. The isomers can be separated by conventional procedures.

The oximes of formula II which are utilized as starting materials in Procedures A, B and C above are novel. They can be prepared by nitrosating a thiazoline or 5,6-dihydro-2H-1,4-thiazine of the formula

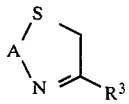    VII wherein A and $R^3$ are as defined above,
conveniently in the presence of a diluent.

The nitrosation is conveniently effected by conventional procedures, e.g. using a nitrite, e.g. an alkali metal nitrite such as sodium nitrite, with addition of an acid such as acetic acid, propionic acid, a mixture of acetic acid and acetic anhydride, or an aqueous mineral acid such as hydrochloric acid. Nitrogen tetroxide, nitrosyl chloride and alkyl nitrites such as methyl nitrite, ethyl nitrite or isopentyl nitrite can also be used as the nitrosating compounds. These latter compounds can be reacted not only in acidic but also in alkaline medium.

Diluents for this reaction include water, alcohols, acetonitrile, aromatic hydrocarbons, chlorinated hydrocarbons as well as ethers.

The reaction is conveniently carried out at temperatures between −20° C. and 100° C., and, preferably, between 0° C. and 60° C.

For the isolation of the compounds of formula II, the solvent can be removed, e.g. by filtration or distillation, and the residue can either be washed, e.g. with water, dried and crystallized or purified chromatographically, or can be taken up in a suitable solvent, washed with water, the solution dried over a suitable drying agent, e.g. anhydrous sodium sulfate, and, after distilling off the solvent, the product can be recrystallized or purified chromatographically.

The thiazolines of formula VII wherein A is a group (a), which are utilized as starting materials, are either known as can be prepared according to known methods, e.g. in accordance with F. Asinger et al., Ann. 610, 17–24 and 33–49 (1957), Angew. Chemie 79, 953 (1967) or DOS No. 2 645 731.

The 5,6-dihydro-2H-1,4-thiazines of formula VII wherein A is the group (b), which are also utilized as starting materials, are likewise partly known (e.g. from Ann. 652, 50 (1962) and Asinger et al., Monatsheft für Chemie 102, 321–332 (1971)), or can be prepared analogous to known methods. The following Process Scheme represents a general preparation process:

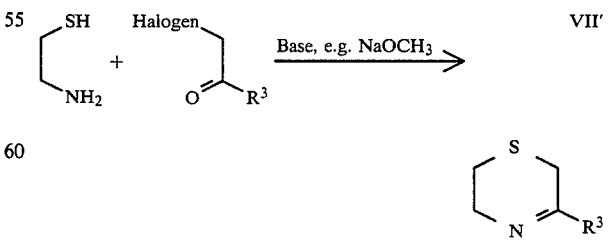

Since the 5,6-dihydro-2H-1,4-thiazines of formula VII' are very sensitive to auto-oxidation in air and are converted thereby into corresponding sulfoxides and sulfones, it is convenient to convert the 5,6-dihydro-2-H-

1,4-thiazine compound without isolation directly into the corresponding oxime of formula II wherein A signifies the group (b) by a one-pot process. The reaction with a nitroso compound can be carried out as described above, preferably with the use of an alkyl nitrite in alkaline medium.

The oximes of formula II, which are utilized as starting materials in Procedures A, B and C, can also be prepared from glyoxyl hydroxamic acid chloride or an alkyl or cycloalkyl derivative thereof and the corresponding mercaptoamine of the formula H$_2$N—A—SH, according to the following Process Scheme:

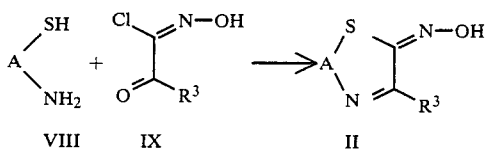

the reaction is conveniently effected in an inert diluent, in the presence of an acid-binding agent and in a temperature range from $-30°$ C. to room temperature. The diluents for this reaction include inert organic solvents. Preferred solvents are ethers and ether-like compounds such as diethyl ether and tetrahydrofuran; pyridine; acetonitrile; alcohols; and water.

Preferred acid-binding agents are alkali carbonates such as sodium carbonate, potassium carbonate and sodium bicarbonate, lower alkylamines such as triethylamine; and pyridine.

The isocyanates of formula III are either known or can be prepared according to known methods, e.g. by reaction of the respective amine R$^5$NH$_2$ with phosgene and subsequent heating. Examples of such known isocyanates are methyl isocyanate, ethyl isocyanate, isopropyl isocyanate, tert.-butyl isocyanate, allyl isocyanate, cyclopropyl isocyanate and cyclohexyl isocyanate.

The carbamoyl halides of formula IV are likewise either known or can be prepared according to known methods, e.g. by reaction of the respective amine R$^4$R$^5$NH with phosgene. Examples of such known carbamoyl halides are dimethylcarbamoyl chloride, methylethylcarbamoyl chloride, N-methyl-N-trichloromethylsulphenyl-carbamoyl fluoride, N-methyl-N-fluorodichloromethylsulphenyl-carbamoyl fluoride, N-methyl-N-chlorodifluoromethylsulphenyl-carbamoyl fluoride, N-methyl-N-(3-trifluoromethylphenylsulphenyl)-carbamoyl fluoride, N-acetyl-N-methylcarbamoyl chloride, N-methyl-N-(4-chlorophenylsulphenyl)-carbamoyl fluoride, N-methyl-N-(morpholin-1-ylsulphenyl)-carbamoyl fluoride and N-methyl-N-(tert.-butylthio)sulphenylcarbamoyl fluoride.

The amines of formula V are likewise either known or can be prepared according to known methods. Examples of such known amines are methylamine, ethylamine, dimethylamine, methylethylamine and allylmethylamine.

The sulphenyl chlorides of formula VI are likewise either known or can be prepared according to known methods. Examples of such known sulphenyl chlorides are methylsulphenyl chloride, trichloromethylsulphenyl chloride, dichlorofluoromethylsulphenyl chloride, chlorodifluoromethylsulphenyl chloride, trifluoromethylsulphenyl chloride, phenylsulphenyl chloride, 2,4-dichlorophenylsulphenyl chloride, 3-trifluoromethylphenylsulphenyl chloride, 3-methylphenylsulphenyl chloride, 4-chloro-3-trifluoromethylphenylsulphenyl chloride, sulfur dichloride and sulfur monochloride.

The compounds of this invention are active as pesticides and, in particular, for the control of insects, mites, nematodes and molluscs.

They are especially valuable against:

(a) Coleoptera such as e.g. Epilachna spp., *Leptinotarsa decemlineata*, Anthonomus spp., *Conotrachelus nenuphar*, Lema spp., *Lissorhoptrus oryzaephilus*, Phyllotreta spp., *Psylliodes chrysocephala, Meligethes aenus, Ceutorrhynchus assimilia*, Agriotes spp., *Otiorhynchus sulcatus, Melolontha melolontha* and Diabrotics spp., (b) Lepidoptera such as e.g. Laspeyresia spp., *Adoxophyes orana, Tortrix viridana, Cheimatobia brumata, Lyonetia clerkella, Operophtera brumata, Lithocolletis blancardella, Porthetria dispar, Mamestra brassicae, Agrotis segetum*, Plutella spp., *Pieris brassicae, Choristoneura fumiferana*, Heliothis spp., Spodoptera spp., *Pectinophora gossipiella*, Chilo spp., *Ostrinia nubilalis, Clysia ambiguella, Lobesia botrana*;

(c) Diptera such as e.g. *Drosophila melanogaster*, Ceratitis spp., *Oscinella frit*, Dacus spp. and Rhagoletis spp. Leatherjacket spp., Sciara spp. Phorbia spp. and *Megasetia agarici*;

(d) Homoptera, i.e. aphids such as e.g. *Aphis fabae, Myzus persicae* and further species of these genera, Rhophalosiphon spp., Schizaphis spp., Dysaphis spp., Eriosoma spp., Macrosiphum spp., Adelges spp., *Sitobion avenae*, Metopolophium spp. as well as shield lice and soft lice such as e.g. Aspidiotus spp., Saissetia spp., *Quadraspidiotus perniciosus, Aonidiella aurantii*, Coccus spp., Lepidosaphes spp., Planococcus spp., Pseudococsus spp., Ceroplastes spp., *Icerya purchasi*, Chrysomphalus spp., Parlatoria spp., Rhizoecus spp. as well as cicades such as e.g. Nephotettix spp., Laodelphax spp., Nilaparvata spp., Sogatella spp. and Erythroneura spp.;

(e) Aleurodidae such as e.g. *Trialeurodes vaporariorum*, Dialeurodes spp., Aleurothrixus spp., Bemisia spp., Aleyrodes spp., moreover species of thrips and bugs;

(f) Acarina such as e.g. *Tetranychus urticae, Panonychus ulmi* and other Tetranychida, Tarsonemida such as Steneotarsonemus spp., Tenuipalpida such as Brevipalpus, Eriophyda such as *Phyllocoptruta oleivora, Aceria scheldoni*, Eriophyes spp., Aceria spp. and further ticks;

(g) Nematoda such as e.g. free-living nematodes (inter alia Pratylenchus spp. such as P. penetrans), leaf-parasitic nematodes (inter alia Aphelenchoides) and root-parasitic nematodes (inter alia Meloidogynae spp. such as M incognita, Globodera spp. such as *G. rostochiensis*); and (h) Mollucsa such as e.g. Deroceras spp.

The compounds of this invention are systemically active and act as contact poisons and feed poisons.

The instant invention is also directed to pesticidal compositions as solutions, emulsions, suspension, powders, pastes and granulates which contain inert carrier materials and, as the active ingredient, one or more of the compounds of formula I.

These compositions are prepared by known methods such as, for example, by mixing the active substance with extenders (liquid solvents, liquified gases under pressure and/or solid carrier substances) and, if desired, surface-active agents (emulsifiers, wetting agents or dispersing agents). When water is used as the extender, organic solvents can also be used as auxiliary solvents.

Examples of liquid solvents include: aromatics such as xylene, toluene and alkyl-naphthalenes; chlorinated aromatics and chlorinated aliphatic hydrocarbons such as chlorobenzenes, chloroethylenes and methylene chloride; aliphatic hydrocarbons such as cyclohexane and paraffins (e.g., petroleum fractions); alcohols such as butanol and glycol as well as their ethers and esters; ketones such as acetone, methyl ethyl ketone, methyl isobutyl ketone and cyclohexanone; strongly polar solvents such as dimethylformamide, N-methylpyrrolidone and dimethylsulfoxide, and water.

Examples of liquified gaseous extenders or carrier substances include liquids which are gaseous at normal temperature and under normal pressure such as aerosol propellants, e.g. halogenated hydrocarbons (e.g. dichlorodifluoromethane).

Examples of solid carrier substances include natural mineral powders such as kaolins, clays, talc, chalk, quartz, attapulgite, montmorillonite and diatomaceous earth, and synthetic mineral powders such as high-dispersible silicic acid, aluminum oxide and silicates.

Surface-active agents, especially emulsifying agents and wetting agents, suitable for use in the pesticidal compositions of this invention can be non-ionic or anionic. Examples of non-ionic emulsifiers which can be used include polyoxyethylene-fatty acid esters, polyoxyethylene-fatty alcohol ethers and alkylaryl-polyglycol ethers. Examples of anionic emulsifiers include alkyl sulfonates, alkyl sulfates and aryl sulfonates.

Examples of dispersing agents include lignin, sulfite lyes and methyl cellulose.

The active ingredients of this invention can be present in the composition in admixture with other known active substances. The compositions generally contain between 0.0005 wt. % and 95 wt. % of total active substances, preferably between 1 wt. % and 75 wt. %.

The pesticidal compositions of the present invention can be in application forms suitable for storage or shipment. In such forms the concentration of active ingredients is normally at the higher end of the above concentration range. These forms can then be diluted with the same or different carrier materials to afford active ingredient concentrations suitable for practical use, and such concentrations normally lie at the lower end of the above-noted concentration range.

The active ingredients can also be used as such in the compositions or in application forms prepared from these compositions such as ready-for-use solutions, emulsions, foams, suspensions, powders, pastes, soluble powders, dusting agents and granulates. They are used in the usual procedures such as squirting, spraying, smokescreening, dusting, scattering, drilling-in, vaporizing, pouring, drenching or incrustating.

The concentrations of active ingredient in the ready-for-use preparations can vary over wide limits. In spray liquors, the concentration lies between 0.0005 wt. % and 20 wt. %.

The active ingredients can also be used with good effect in the ultra-low-volume process (ULV) where it is possible to formulate spray liquors having preferably from 10 to 20 wt. %.

The active ingredients can also be used with good effect in the low-volume process and in the high-volume process where it is possible to formulate spray liquors having from 0.5 to 1.0 or 0.05 to 0.1 wt. % of active ingredient respectively.

In granulates, the concentration of active ingredients is preferably from 2 to 10 wt. %.

The pesticidal compositions of the present invention can contain other active substances, for example, other pesticides, besides the compounds of formula I. Such combination compositions are suitable for increasing the activity or for broadening the spectrum of activity.

In preparing the pesticidal compositions of the present invention, the active ingredient of formula I is mixed with inert carrier material. In the case of pulverous compositions the active ingredient can be mixed with the carrier substances, for example, by grinding together; or the inert carrier material can be impregnated with a solution or suspension of the active ingredient and then the solvent or suspension agent can be removed by evaporation, heating or by sucking-off under reduced pressure. By the addition of wetting and/or dispersing agents such pulverous compositions can be made readily wettable with water so that they can be converted into aqueous suspensions which are suitable as spray compositions. For the manufacture of emulsifiable concentrates, which are especially suitable for storage and shipment, the active ingredient can be mixed, for example, with an emulsifying agent or dissolved in an inert solvent and thereafter mixed with an emulsifier. Ready-for-use emulsions are prepared by diluting such concentrates with water.

The pesticidal compositions of the present invention are used by treating the locus to be protected or the pests themselves with the pesticidal compositions of the present invention. This method of use is preferably carried out by applying the composition to the soil or leaves, depending on the pests to be controlled.

The following Examples serve for the more precise illustration of the invention.

EXAMPLE 1

20.0 g (0.126 mol) of 5-oxo-2,2,4-trimethyl-3-thiazoline oxime are dissolved in 100 ml of chloroform. To the solution are added 15 ml (0.252 mol) of freshly distilled methyl isocyanate as well as 3 drops of triethylamine. The mixture, which warms slightly after a short time, is left to stand at room temperature for 16 hours. Subsequently, the slightly turbid solution is filtered, and the solvent and excess methyl isocyanate are distilled off in vacuo. The oily residue is purified chromatographically on 250 g of silica gel using ethyl acetate/n-hexane (1:1) for the elution. The solvent is removed by evaporation, and the resulting residue is recrystallized from methyl chloride/n-hexane/diethyl ether to yield 5-oxo-2,2,4-trimethyl-3-thiazoline O-(methylcarbamoyl)oxime as white crystals, m.p. 90°–92° C.

EXAMPLE 2

3.0 g (0.019 mol) of 5-oxo-2,2,4-trimethyl-3-thiazoline oxime are added portionwise to a suspension of 0.9 g of sodium hydride in 20 ml of tetrahydrofuran. The sodium hydride was liberated shortly before its use from a 55% suspension in oil by two-fold extraction with a small amount of absolute pentane. After completion of the hydrogen evolution, the mixture is stirred at room temperature for an additional 1 hour. 2.05 g (0.019 mol) of dimethylcarbamoyl chloride are added dropwise, and the reaction mixture is stirred at room temperature for 16 hours. The residue is then taken up in diethyl ether, and the organic phase is washed with saturated sodium chloride solution and dried over anhydrous sodium sulfate. The solvent is subsequently distilled off, and the residue is recrystallized from diethyl ether/n- hexane to yield 5-oxo-2,2,4-trimethyl-3-thiazoline O-(dimethylcarbamoyl)oxime, m.p. 92°–95° C.

EXAMPLES 3–22

Compounds of formula I are prepared from appropriate starting materials of formula II and III according to the procedure described in Example 1. The compounds of formula I are listed in the following Table A.

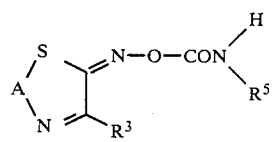

TABLE A

| Example | A | $R^3$ | $R^5$ | M.p. |
|---|---|---|---|---|
| 3 | $(CH_3)(C_2H_5)C{<}$ | $CH_3$ | $CH_3$ | –(oil) |
| 4 | $(C_2H_5)(n\text{-}C_4H_9)C{<}$ | $CH_3$ | $CH_3$ | –(oil) |
| 5 | $(CH_2)_4C{<}$ | $CH_3$ | $CH_3$ | 117–119° C. |
| 6 | $CH_3CH{<}$ | $CH_3$ | $CH_3$ | 112–114° C. |
| 7 | $C_2H_5CH{<}$ | $CH_3$ | $CH_3$ | 109–110° C. |
| 8 | $(CH_3)_2CHCH{<}$ | $CH_3$ | $CH_3$ | 120–123° C. |
| 9 | $(CH_3)(C_2H_5)C{<}$ | H | $CH_3$ | 95–96° C. |
| 10 | $(CH_3)(CH_3)C{<}$ | $C_2H_5$ | $CH_3$ | 102–105° C. |
| 11 | $(CH_3)(CH_3)C{<}$ | $(CH_3)_2CH$ | $CH_3$ | 94–96° C. |
| 12 | $(CH_3)(CH_3)C{<}$ | $CH_3$ | $C_2H_5$ | 95–97° C. |
| 13 | $(CH_3)(C_2H_5)C{<}$ | $CH_3$ | $(CH_3)_2CH$ | 80–81° C. |
| 14 | $-CH_2CH_2-$ | $CH_3$ | $CH_3$ | 143.5° C. (with decomposition) |
| 15 | $-CH_2CH_2-$ | $C_2H_5$ | $CH_3$ | 108–110° C. |
| 16 | $-CH_2CH_2-$ | $(CH_3)_2CH$ | $CH_3$ | 79–80.5° C. |
| 17 | $-CH_2CH_2-$ | ▷– | $CH_3$ | 109–111° C. |

TABLE A-continued

| Example | A | R³ | R⁵ | M.p. |
|---|---|---|---|---|
| 18 | (CH₃)(CH₃)C⟨ | ▷− | CH₃ | 161–163° C. |
| 19 | (▷−)(CH₃)C⟨ | CH₃ | CH₃ | 77–79° C. |
| 20 | (CH₃)(CH₃)C⟨ | CH₃ | CH₂CH=CH₂ | 46–48° C. |
| 21 | (CH₃)(CH₃)C⟨ | CH₃ | ▷− | 77–78° C. |
| 22 | (C₂H₅)(C₂H₅)C⟨ | CH₃ | CH₃ | 48–50° C. |

EXAMPLE 23

2-Oxo-5,6-dihydro-3-methyl-2H-1,4-thiazine oxime is reacted with dimethylcarbamoyl chloride as described in Example 2 to yield 2-oxo-5,6-dihydro-3-methyl-2H-1,4-thiazine O-(dimethylcarbamoyl)oxime, m.p. 64°–65° C.

EXAMPLE 24

3.2 g (0.015 mol) of 5-oxo-2,2,4-trimethyl-3-thiazoline O-(methylcarbamoyl)oxime are dissolved in 15 ml of absolute methylene chloride and treated dropwise at 0° C. with stirring with 1.2 ml of pyridine and 0.55 ml (0.086 mol) of freshly distilled sulfur dichloride. The mixture is allowed to come to room temperature slowly and then stirred for 16 hours. The mixture is diluted with 100 ml of methylene chloride, washed once with dilute hydrochloric acid and twice with semi-saturated sodium chloride solution and dried over anhydrous sodium sulfate. After the solvent is distilled off, the oily residue is purified by means of two-fold chromatography on silica gel (eluent 7% acetone in chloroform; 40% toluene in ethyl acetate). Recrystallizations from acetone/n-hexane yield N,N'-bis-[2,2,4-trimethyl-3-thiazolin-5-O-(methylcarbamoyl)oximino]sulfide, m.p. 152°–154° C.

EXAMPLE 25

3.0 g (0.019 mol) of 5-oxo-2,2,4-trimethyl-3-thiazoline oxime are suspended in 10 ml of absolute acetonitrile. To the suspension at 0° C. there are successively added 5.5 g of anhydrous potassium carbonate and, dropwise, a solution of 4.52 g of N-(di-n-butylaminosulphenyl)-N-methylcarbamoyl fluoride in 10 ml of absolute acetonitrile. The reaction mixture is allowed to stir well at room temperature for 20 hours. Subsequently, the precipitated potassium salt is filtered off, and the filtrate is evaporated. Chromatography of the crude oily product on silica gel with ethyl acetate/toluene (1:3) as the eluent yields 5-oxo-2,2,4-trimethyl-3-thiazoline O-[N-(di-n-butylaminosulphenyl)-N-methylcarbamoyl]oxime, $n_D^{20}$ 1.5200.

EXAMPLES 26–30

In a manner analogous to the method described in Example 25, 5-oxo-2,2,4-trimethyl-3-thiazoline oxime and the appropriate starting material of formula IV are reacted to produce the compounds of the formula I given in the following Table B.

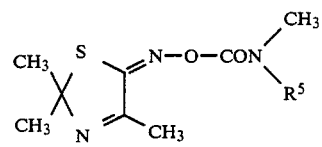

TABLE B

| Example | R⁵ | M.p. | $n_D^{20}$ |
|---|---|---|---|
| 26 | S—N⟨O⟩ (morpholino) | 103–104° C. | — |
| 27 | S—S—CH(CH₃)₂ | — | 1.5590 |
| 28 | S—S—C(CH₃)₃ | 74–76° C. | — |
| 29 | S—CCl₃ | 90–93° C. | — |
| 30 | S—C₆H₄—Cl | 144–146° C. | — |

EXAMPLE 31

2-Oxo-5,6-dihydro-3-isopropyl-2H-1,4-thiazine oxime is reacted with N-methyl-N-morpholinosulphenylcarbamoyl fluoride as described in Example 25 to yield 2-oxo-5,6-dihydro-3-isopropyl-2H-1,4-thiazine O-(N-methyl-N-morpholinosulphenylcarbamoyl)oxime, m.p. 127°–128.5° C.

EXAMPLE 32

8.3 ml of triethylamine are added dropwise to a suspension of 8.59 g of 5-oxo-2,2,4-trimethyl-3-thiazoline oxime in a solution of 10.0 g of bis-(N-methyl-N-fluorocarbonylamino)sulfide in 100 ml of absolute toluene, cooled to −50° C. The resulting clear solution is allowed to warm slowly to 0° C. during 1½ hours, during which time a crystalline product is precipitated. The reaction mixture is poured into ice-cold brine and extracted with ethyl acetate. After drying the organic phase over anhydrous sodium sulfate and evaporating it, the resulting residue is purified by chromatography on silica gel (eluent:ethyl acetate/n-hexane 1:1). Crystallization from ethyl acetate/n-hexane yields 5-oxo-2,2,4-trimethyl-3-thiazoline O-[N-(N-methylfluoroformamidothio)-N-methylcarbamoyl]oxime, m.p. 77°–79° C.

1.13 g of the product of the previous stage and 0.61 g of 2-oxo-5,6-dihydro-3-isopropyl-2H-1,4-thiazine oxime are suspended in 25 ml of absolute toluene at 0° C. The suspension is treated with 0.57 g of triethylamine, and the reaction mixture is stirred and slowly warmed to room temperature during 16 hours. The mixture is worked up as described for the previous stage. Crystallization from ethyl acetate/n-hexane yields the O,O'-[thiobis(methyliminocarbonyl)]dioxime of 5-oxo-2,2,4-trimethyl-3-thiazoline and 2-oxo-5,6-dihydro-3-isopropyl-2H-1,4-thiazine, m.p. 141.5°–143.5° C.

PREPARATION OF THE STARTING MATERIALS

EXAMPLE 33

The 5-oxo-2,2,4-trimethyl-3-thiazoline oxime required as the starting material in Examples 1, 2, 12, 20, 21, 25–30 and 32 is prepared as follows:

32.0 g (0.46 mol) of sodium nitrite are suspended in a solution of 30.0 g (0.232 mol) of 2,2,4-trimethyl-3-thiazoline dissolved in 200 ml of acetonitrile. Then, there are added dropwise to the suspension, cooled to −10° C., with stirring 26.6 ml (0.464 mol) of acetic acid and subsequently 21.9 ml (0.232 mol) of acetic anhydride. After completion of the addition, the reaction mixture is warmed to 0° C. and stirred at room temperature for an additional 3 hours.

The reaction mixture is then partially concentrated in vacuo, the residue is treated with about 500 ml of water and sufficient solid sodium bicarbonate is added to the mixture to afford pH 6. After three-fold extraction with 200 ml of chloroform each time, the extracts are washed with water, the organic phase is dried over anhydrous sodium sulfate, and the phase is concentrated in vacuo until it is turbid. The organic phase is filtered, and the filtrate is treated with n-hexane. 5-oxo-2,2,4-trimethyl-3-thiazoline oxime precipitates as light brown crystals and is filtered off. Two recrystallizations from chloroform/n-hexane yield a product which melts at 161°–163° C.

EXAMPLE 34

The 5-oxo-2,2,4-trimethyl-3-thiazoline oxime can also be prepared as follows:

30.0 g (0.232 mol) of 2,2,4-trimethyl-3-thiazoline and 17.6 g (0.255 mol) of sodium nitrite are dissolved in 75 ml of water and 26.6 ml (0.464 mol) of acetic acid are added dropwise, with stirring at 45° C. The internal temperature of the reaction mixture is allowed to rise slowly to 10°–15° C., and the mixture is then stirred at this temperature for an additional 2 hours. The product precipitates as ochre-brown crystals and is filtered, washed with water and dried in vacuo. A single recrystallization from chloroform/n-hexane yields 5-oxo-2,2,4-trimethyl-3-thiazoline oxime, m.p. 159°–161° C.

EXAMPLES 35–46

The corresponding substituted 3-thiazolines are reacted with sodium nitrite analogous to the process described in Example 33 or 34 in order to prepare the starting materials of formula II listed in the following Table C. The corresponding end products of formula I are also given in this Table.

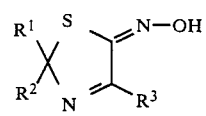

TABLE C

| Example | R¹ | R² | R³ | M.p. | Example No. of the end-product of formula I |
|---|---|---|---|---|---|
| 35 | CH₃ | C₂H₅ | CH₃ | — (not purified) | 3, 13 |
| 36 | C₂H₅ | n-C₄H₉ | CH₃ | —(oil) | 4 |
| 37 | —(CH₂)₄— | | CH₃ | 157–159° C. | 5 |
| 38 | H | CH₃ | CH₃ | 145–148° C. | 6 |
| 39 | H | C₂H₅ | CH₃ | 115–118° C. | 7 |
| 40 | H | (CH₃)₂CH | CH₃ | — (not purified) | 8 |
| 41 | CH₃ | C₂H₅ | H | — (not purified) | 9 |
| 42 | CH₃ | CH₃ | C₂H₅ | — (not purified) | 10 |
| 43 | CH₃ | CH₃ | (CH₃)₂CH | 187–192° C. | 11 |
| 44 | CH₃ | CH₃ | ▷– | 180–181.5° C. | 18 |
| 45 | CH₃ | ▷– | CH₃ | — (not purified) | 19 |
| 46 | C₂H₅ | C₂H₅ | CH₃ | — (not purified) | 22 |

EXAMPLE 47

The 2-oxo-5,6-dihydro-3-isopropyl-2H-1,4-thiazine oxime required as the starting material in Examples 16, 31 and 32 is prepared as follows:

18.4 g (0.80 mol) of sodium are dissolved in 400 ml of absolute methanol. Dry cysteamine is added portionwise to the solution with the exclusion of air, and the mixture is stirred until a clear solution is obtained. The reaction mixture is warmed briefly at 55° C. Subsequently, 132 g (0.80 mol) of 1-bromo-3-methyl-2-butanone are added dropwise thereto while the internal temperature is held at 30° C. by cooling with ice water. The reaction mixture is stirred at room temperature for an additional 30 minutes.

Then, a solution of 18.4 g (0.80 mol) of sodium in 400 ml of methanol is added to the reaction mixture, and, after 10 minutes, the mixture is treated dropwise with 106.4 ml (0.80 mol) of isopentyl nitrite. The internal temperature of the reaction mixture thereby rises to 56° C. within 50 minutes. The mixture is allowed to stir at room temperature for 16 hours and is then treated with 2.3 liters of water. The aqueous mixture is filtered through Celite, and the clear filtrate is treated, with stirring and cooling, with 45.6 ml (0.80 mol) of acetic acid to obtain pH 6. After 30 minutes, the precipitated crystals are filtered off, washed with a large amount of water and subsequently with cold isopropanol, and dried to yield 2-oxo-5,6-dihydro-3-isopropyl-2H-1,4-thiazine oxime as crystals, m.p. 167°–169° C.

EXAMPLES 43–50

The starting materials of formula II listed in the following Table D are prepared from corresponding starting materials analogously to the process described in Example 47. The corresponding end products of formula I are also listed in this Table.

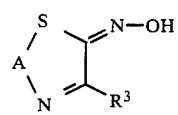

TABLE D

| Example | $R^3$ | M.p. | Example No. of the end product of formula I |
|---|---|---|---|
| 48 | $CH_3$ | 197° C. (with | 14, 23 |
| 49 | $C_2H_5$ | 155–157° C. | 15 |
| 50 | 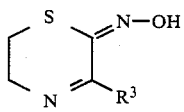 | 155–157° C. | 17 |

EXAMPLE 51

The 2-oxo-5,6-dihydro-3-methyl-2H-1,4-thiazine oxime required as the starting material in Examples 14 and 23 can also be manufactured as follows:

2.27 g (0.02 mol) of cysteamine hydrochloride are suspended in 40 ml of absolute tetrahydrofuran and treated with 5.55 ml (0.04 mol) of triethylamine to free the base. The mixture is stirred for 15 minutes at room temperature and then cooled down to about −30° C. At this temperature a solution of 2.42 g (0.02 mol) of pyruvyl chloride 1-oxime in 10 ml of absolute tetrahydrofuran is added dropwise. The reaction mixture is allowed to warm to room temperature while being well stirred. After two hours ice-water and then dilute hydrochloric acid are added until a pH of 5–6 has been attained. The reaction mixture is extracted twice with ethyl acetate and the organic phase is washed with sodium chloride solution, dried over anhydrous sodium sulfate and finally evaporated. The resulting crystalline residue is treated with active charcoal. After recrystallization from hot ethyl acetate and n-hexane there is obtained pure 2-oxo-5,6-dihydro-3-methyl-2H-1,4-thiazine oxime, m.p. 197° C. (with decomposition).

EXAMPLE 52

This example illustrates compositions containing a compound of formula I as the active ingredient:

|  | g/liter |
|---|---|
| (a) Active Ingredient, a compound of formula I | 250 |
| N—Methyl-2-pyrrolidone | 500 |
| Emulsifier mixture consisting of: | |
| Calcium alkylarylsulfonate, alkylphenol ethoxylate, block polymerisate of propylene oxide and ethylene oxide | 50 |
| Calcium dodecylbenzene sulfonate | 25 |
| Solvent (mixture of mono-, di- and tri-lower alkylbenzenes) | ad 1000 ml |
| (b) Active Ingredient, a compound of formula I | 500 |
| N—Methyl-2-pyrrolidone | ad 1000 ml |
| (c) Active Ingredient, a compound of formula I | 50 g |
| High-dispersible silicic acid | 5 g |
| Sodium lauryl sulfate | 1 g |
| Sodium lignosulfonate | 2 g |
| Kaolin | 42 g |
|  | 100 g |

We claim:

1. A compound of the formula

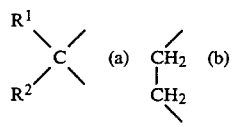 II wherein A is a group (a) or (b)

$$\begin{array}{cc} R^1 \diagdown \diagup \\ \diagup C \diagdown \text{(a)} \quad \begin{array}{c} \diagup \\ CH_2 \text{ (b)} \\ | \\ CH_2 \\ \diagdown \end{array} \\ R^2 \end{array}$$

$R^1$ and $R^2$ are hydrogen, lower alkyl or cycloalkyl, or together with the carbon atom to which they are attached a 4- to 6-membered, saturated hydrocarbon ring and $R^3$ is hydrogen, lower alkyl or cycloalkyl.

2. A compound accordiung to claim 1, wherein A is a group (a) and $R^1$ is hydrogen or lower alkyl.

3. A compound according to claim 2, wherein $R^2$ in the group (a) is hydrogen or lower alkyl.

4. A compound according to any one of claims 1–3, wherein A is a group (a) and $R^3$ is methyl.

5. A compound according to claim 1, 5-oxo-2,2,4-trimethyl-3-thiazoline oxime.

6. A compound according to claim 1, 2-oxo-5,6-dihydro-3-isopropyl-2H-1,4-thiazin oxime.

* * * * *